(12) United States Patent
Davis et al.

(10) Patent No.: US 6,336,935 B1
(45) Date of Patent: Jan. 8, 2002

(54) DISPOSABLE THERMAL BODY WRAP

(75) Inventors: Leane Kristine Davis, Milford; Nancy Jean McCarthy, Cincinnati, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/397,338

(22) Filed: Sep. 15, 1999

(51) Int. Cl.⁷ .................................................. A61B 7/02
(52) U.S. Cl. ........................ 607/112; 607/114; 607/96
(58) Field of Search ................... 607/112, 114, 607/96

(56) References Cited

U.S. PATENT DOCUMENTS

| | | | |
|---|---|---|---|
| 2,547,886 A | 4/1951 | Poux | 62/1 |
| 2,562,121 A | 7/1951 | Poux | 150/2.2 |
| 2,602,302 A | 7/1952 | Poux | 62/1 |
| 3,463,161 A | 8/1969 | Andrassy | 128/402 |
| 3,900,035 A | 8/1975 | Welch et al. | 128/402 |

(List continued on next page.)

FOREIGN PATENT DOCUMENTS

| | | | | |
|---|---|---|---|---|
| EP | 0 370 600 A1 | 7/1989 | | F24J/1/00 |
| GB | 2 205 496 A | 12/1988 | | A61F/7/03 |
| GB | 2 297 490 A | 8/1996 | | A61F/7/03 |
| IN | 160443 | 9/1983 | | C09K/3/02 |
| JP | SHO 56-145846 | 11/1981 | | A61F/7/03 |
| JP | SHO 57-170252 | 10/1982 | | A61F/7/03 |
| JP | SHO 58-37075 | 3/1983 | | C09K/5/00 |
| JP | HEI 3-100090 | 4/1991 | | C09K/5/00 |
| JP | HEI 5-317188 | 12/1993 | | A47J/36/28 |
| JP | HEI 6-1969 | 1/1994 | | C09K/5/00 |
| JP | HEI 6-315498 | 11/1994 | | A61F/7/08 |
| JP | HEI 6-343658 | 12/1994 | | A61F/7/08 |
| JP | HEI 7-67907 | 3/1995 | | A61F/7/08 |
| JP | HEI 7-49042 | 5/1995 | | A61F/7/08 |
| JP | HEI 7-112006 | 5/1995 | | A61F/7/08 |
| JP | HEI 7-124192 | 5/1995 | | A61F/7/08 |
| JP | HEI 7-194641 | 8/1995 | | A61F/7/08 |
| JP | HEI 7-194642 | 8/1995 | | A61F/7/08 |
| JP | HEI 8-80317 | 3/1996 | | A61F/7/08 |
| JP | HEI 8-98856 | 4/1996 | | A61F/7/08 |
| JP | HEI 8-126656 | 5/1996 | | A61F/7/08 |
| WO | WO 94/00087 | 1/1994 | | A61F/7/00 |

OTHER PUBLICATIONS

U.S. application No. 08/777,853, Cramer, et al., filed Dec. 31, 1996, Pat. No. 6020040.
U.S. application No. 08/777,642, Cramer, et al., filed Dec. 31, 1996, Pat. No. 6102937.
U.S. application No. 08/777,856, Cramer, et al., filed Dec. 31, 1996, Pat. No. 6096067.
U.S. application No. 08/680,472, Ouellette, et al., filed Jul. 15, 1996, Pat. No. 6074505.
U.S. application No. 08/984,009, Davis, et al., filed Dec. 3, 1997, Pat. No. 6146732.
U.S. application No. 08/984,366, Davis, et al., filed Dec. 3, 1997, Pat. No. 6048326.
U.S. application No. 08/915,831, Barone, et al., filed Aug. 21, 1997, Pat. No. 6090234.

*Primary Examiner*—Linda C. M. Dvorak
*Assistant Examiner*—Jocelyn Ram
(74) *Attorney, Agent, or Firm*—Loy M. White; John M. Howell; Karen F. Clark (57) ABSTRACT

The thermal body wraps of the present invention comprise a unified laminate structure having at least one continuous layer of a flexible material having a substantially rectangular, dog bone-like shape and having a first side, a second side, a first end, a second end, a plurality of heat cells, and means for releasably attaching the thermal body wrap to a user's body. Preferably the heat cells are placed into positions fixed within or to the unified structure of the thermal body wraps, relative to each other and sufficiently close to provide controlled, sustained, and uniform heat to the body or body part of the user.

12 Claims, 2 Drawing Sheets

U.S. PATENT DOCUMENTS

| | | | |
|---|---|---|---|
| 4,095,583 A | 6/1978 | Petersen et al. | 126/263 |
| 4,205,685 A | 6/1980 | Yoshida et al. | 128/399 |
| 4,255,157 A | 3/1981 | Yamaguchi et al. | 44/3 C |
| 4,268,272 A | 5/1981 | Taura | 44/3 R |
| 4,282,005 A | 8/1981 | Sato et al. | 44/3 R |
| 4,366,804 A | 1/1983 | Abe | 126/263 |
| 4,516,564 A | 5/1985 | Koiso et al. | 126/263 |
| 4,517,972 A * | 5/1985 | Finch, Jr. | 128/156 |
| 4,522,190 A | 6/1985 | Kuhn et al. | 126/263 |
| RE32,026 E | 11/1985 | Yamashita et al. | 126/263 |
| 4,575,097 A | 3/1986 | Brannigan et al. | 128/402 |
| 4,649,895 A | 3/1987 | Yasuki et al. | 126/268 |
| 4,756,299 A | 7/1988 | Podella | 126/263 |
| 4,860,748 A | 8/1989 | Chiurco et al. | 128/399 |
| 4,886,063 A | 12/1989 | Crews | 128/403 |
| 4,925,743 A | 5/1990 | Ikeda et al. | 428/702 |
| 4,995,126 A | 2/1991 | Matsuda | 5/421 |
| 5,025,777 A | 6/1991 | Hardwick | 126/263 |
| 5,046,479 A | 9/1991 | Usui | 126/204 |
| 5,062,269 A | 11/1991 | Siegel | 62/4 |
| 5,125,392 A | 6/1992 | Hardwick | 126/263 |
| 5,179,944 A | 1/1993 | McSymytz | 128/403 |
| 5,190,033 A | 3/1993 | Johnson | 128/403 |
| 5,233,981 A | 8/1993 | Miyashita | 607/114 |
| 5,342,412 A | 8/1994 | Ueki | 607/114 |
| 5,366,491 A | 11/1994 | Ingram et al. | 607/108 |
| 5,366,492 A | 11/1994 | Ueki | 607/114 |
| 5,405,671 A | 4/1995 | Kamin et al. | 428/69 |
| 5,674,270 A | 10/1997 | Viltro et al. | 607/112 |
| 5,728,058 A | 3/1998 | Ouellette et al. | 602/62 |
| 5,728,146 A | 3/1998 | Burkett et al. | 607/109 |
| 5,735,889 A * | 4/1998 | Burkett et al. | 607/96 |
| 5,741,318 A | 4/1998 | Ouellette et al. | 607/108 |
| 5,860,945 A | 1/1999 | Cramer et al. | 602/62 |
| 5,904,710 A | 5/1999 | Davis et al. | 607/108 |
| 5,906,637 A | 5/1999 | Davis et al. | 607/108 |
| 5,913,849 A * | 6/1999 | Sundstrom et al. | 604/291 |
| 5,918,590 A * | 7/1999 | Burkett et al. | 126/263.02 |
| 5,925,072 A | 7/1999 | Cramer et al. | 607/108 |
| 5,954,680 A * | 9/1999 | Augustine | 602/42 |
| 5,984,995 A * | 11/1999 | White | 75/230 |

* cited by examiner

DISPOSABLE THERMAL BODY WRAP

BACKGROUND OF THE INVENTION

A common method of treating acute, recurrent, and/or chronic pain is by the topical application of heat to the afflicted area. Such heat treatments are used as a means of therapy for conditions which include aches, stiffness in muscles and joints, nerve pain, rheumatism and the like. Typically, the method for relieving pain using heat treatments has been to topically apply a relatively high heat, i.e., greater than about 40° C., for a short period of time. These treatments include the use of whirlpools, hot towels, hydrocollators, hot water bottles, hot packs, heating wraps and elastic compression bands. Many of these devices employ reusable thermal packs containing, e.g., water and/or microwaveable gels, or electric current. In general, most of these devices are inconvenient to use on a regular and extended basis. The heat energy may not be immediately available when needed, and/or released in a controllable manner, and/or maintained at a consistent temperature over long periods of time. Typically, these types of devices restrict the movements of the user and proper positioning of the thermal energy may not be maintainable during use.

Disposable heat packs based on iron oxidation, such as those described in U.S. Pat. Nos. 4,366,804, 4,649,895, 5,046,479 and Re. 32,026, are known. While these heat packs are more portable than the above described devices, such heat packs have proven not totally satisfactory because many of these heat packs are bulky, cannot maintain a consistent and controlled temperature, and have unsatisfactory physical dimensions, which hinder their effectiveness. Specifically, such devices cannot easily and/or comfortably conform to various body contours, and hence, they deliver short duration, inconsistent, inconvenient and/or uncomfortable heat application directly to the body.

Based on the forgoing, there has been a long felt need for thermal body wraps which reach their operating temperature range relatively quickly, maintain a controlled and sustained temperature, have good overall drapability, adapt to a wide variety of body contours, and releasably attach to the user's body, to provide consistent, convenient and comfortable heat application to the body or body part of the user.

SUMMARY OF THE INVENTION

The thermal body wraps of the present invention comprise a unified laminate structure having at least one continuous layer of a flexible material having a substantially rectangular, dog bone-like shape and having a first side, a second side, a first end, a second end, a plurality of heat cells, and means for releasably attaching the thermal body wrap to a user's body. The heat cells preferably comprise an oxygen activated, heat generating chemistry of powdered iron, powdered activated charcoal, water, and salt, spaced apart and fixed within or to the unified structure of the thermal body wrap. Preferably the heat cells are placed into positions fixed within or to the unified structure of the thermal body wraps, relative to each other and sufficiently close to provide controlled, sustained, and uniform heat to the body or body part of the user.

These and other features, aspects, and advantages of the present invention will become evident to those skilled in the art from a reading of the present disclosure.

All percentages and ratios used herein are by weight of the total composition, and all measurements made at 25° C., unless otherwise specified.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

The present invention relates to disposable thermal body wraps having a unified structure of one or more continuous layers of a flexible material and a plurality of individual heat cells, which preferably contain an oxygen-activated exothermic composition. The heat cells are spaced apart and fixed within or to the unified structure of the thermal body wraps, relative to each other and sufficiently close to provide controlled, sustained, and uniform heat to the body or body part of the user. The disposable thermal body wraps of the present invention further having a substantially rectangular, dog bone-like shape with a first side, a second side, a first end, a second end, and means for releasably attaching the thermal body wrap to a user's body.

In a preferred embodiment of the present invention, at least one of the one or more continuous layers is preferably semirigid when at room temperature, i.e., about 25° C., or below, but softens and becomes substantially less rigid when heated to about 35° C., or greater. Therefore, when the heat cells, which are fixed within or to the unified structure of the thermal body wrap, are active, that is at a heat cell temperature of about 35° C. or greater, the narrow portion of the continuous layer or layers of material immediately surrounding each heat cell preferably softens and acts as a hinge between the heat cells and between any remaining, more rigid portions of the continuous layer or layers, bending preferentially more than either the heat cells or any cooler, more rigid portions. This results in thermal body wraps which possess sufficient rigidity to maintain structural support of the heat cells and prevent unacceptable stretching of structures of the continuous layer or layers during processing or use, while still maintaining good overall drape characteristics when heated. The disposable thermal body wraps of the present invention provide consistent, convenient, and comfortable heat application, and an excellent conformity with user's body, while retaining sufficient rigidity to deter easy access to heat cell contents.

Herein, "comprising" means that other steps and/or other ingredients which do not affect the end result can be added. This term encompasses the terms "consisting of" and "consisting essentially of".

Herein, "disposable", means that, while the thermal body wraps of the present invention may be stored in a resealable, substantially air-impermeable container and reapplied to the user's body as often as required for the relief of pain, they are intended to be thrown away, i.e., deposited in a suitable trash receptacle, after the heat source, i.e., the heat cell(s) or thermal pack(s), has been fully expended.

Herein, "heat cells", means a unified structure, comprising an exothermic composition, preferably a specific iron oxidation chemistry, enclosed within two layers, wherein at least one layer is oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps and the like. Body wraps incorporating heat cells and/or thermal packs adapt to a wide variety of body contours, thus providing consistent, convenient, and comfortable heat application. The preferred heat cells are described in U.S. Pat. No. 5,918,590 and pending U.S. patent application Ser. No. 08/623,752, both of which are assigned to The Procter & Gamble Co., Cincinnati, Ohio. The preferred thermal packs include a unified structure having at least one continuous layer of material and a plurality of heat cells spaced apart and fixed within or to the unified structure of the thermal pack. The thermal packs are described in pending U.S. patent application Ser. Nos. 08/777,853 and 08/984,009, both of which are assigned to The Procter & Gamble Co., Cincinnati, Ohio.

Herein, "plurality of heat cells", means more than one heat cell.

Herein, "continuous layer or layers", means one or more layers of a material which may be uninterrupted or partially, but not completely, interrupted by another material, holes, perforations, and the like, across its length and/or width.

Herein, "rigid", means the property of a material wherein the material may be flexible, yet is substantially stiff and unyielding, and which does not form fold lines in response to gravitational pull or other modest forces.

Herein, "semirigid material", means a material which is rigid to some degree or in some parts, i.e., having at least two-dimensional drape at a temperature of about 25° C., and exhibits a toughness to maintain structural support of the heat cells in an unsupported format, and/or prevent unacceptable stretching of structures of the material during processing or use, while still maintaining good overall drape characteristics when heated, and/or retaining sufficient rigidity to deter easy access to deter easy access to heat cell contents.

Herein, "two dimensional drape", means drape which occurs across a continuous layer or layers, across a thermal pack, or across a select region of a layer or layers, or thermal pack, exclusively along one axis, i.e., one fold line forms, at the expense of other axes in response to gravitational pull or other modest forces.

Herein, "three dimensional drape", means drape which simultaneously occurs across a continuous layer or layers, across a thermal pack, or across a select region of a layer or layers, or thermal pack, along two or more axes, i.e., two or more fold lines form, in response to gravitational pull or other modest forces.

Herein, "fold lines", means the line along which a material forms a temporary or permanent crease, ridge, or crest in response to gravitational pull or other modest forces.

All cited references are incorporated herein by reference in their entireties, unless otherwise specified. Citation of any reference is not an admission regarding any determination as to its availability as prior art to the claimed invention.

All percentages are by weight of total composition, all ratios are weight ratios, and all measurements are made at 25° C., unless otherwise specified.

It is understood that the disposable thermal body wraps of the present invention may comprise one or more heat cells or thermal packs. For clarity, one preferred embodiment of a disposable thermal body wrap comprising a single thermal pack having a plurality of individual heat cells will be described herein. All aspects of other embodiments of the present invention are the same or similar to the embodiment(s) described herein.

Figure 1:
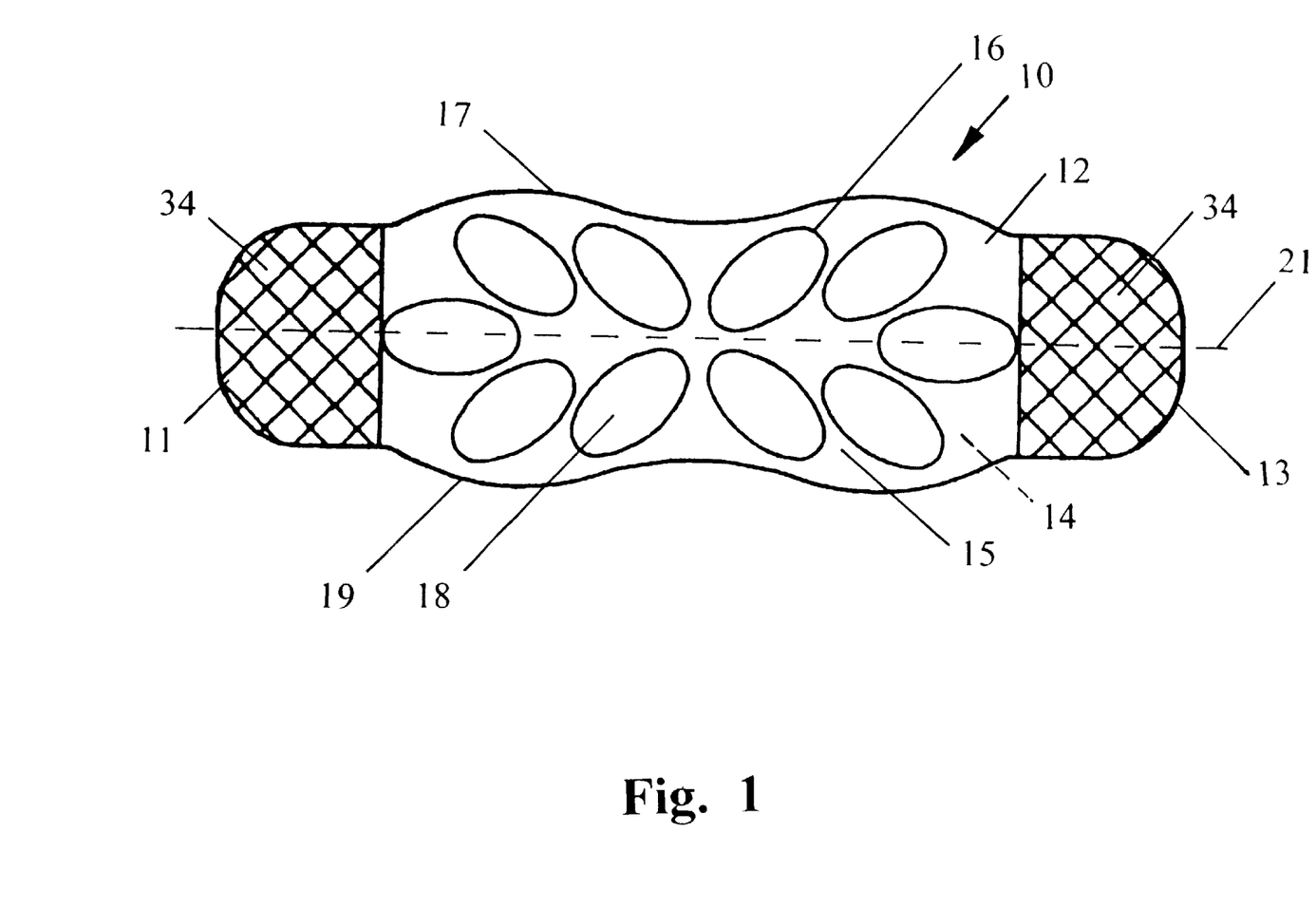
FIG. 1 is a plan view of a preferred embodiment of the disposable thermal body wrap of the present invention, disclosing a pattern of heat cells and adhesive patches on first and second ends.
Figure 2:
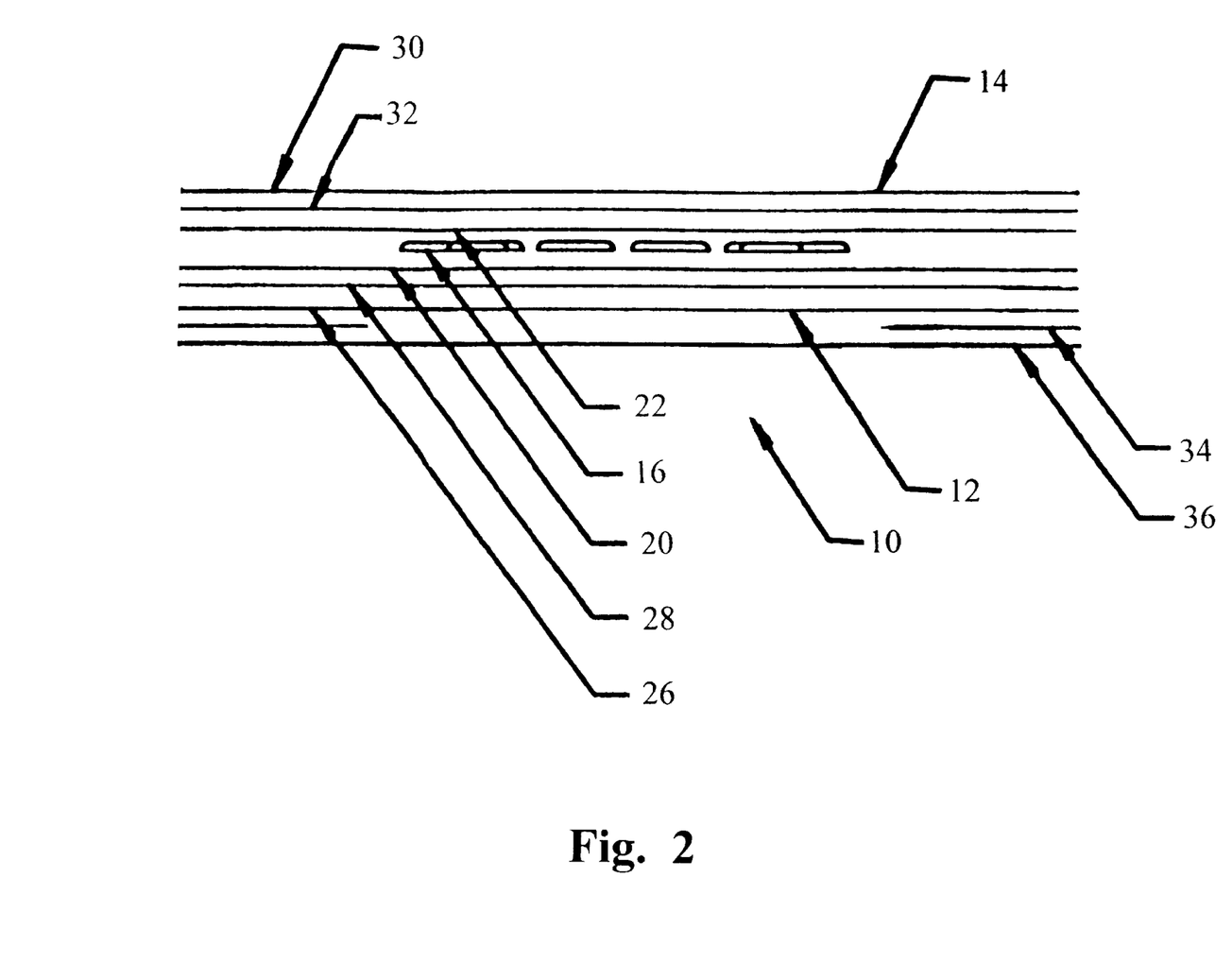
FIG. 2 is sectioned side elevation of FIG. 1.

Referring now to FIGS. 1 and 2, there is shown a preferred embodiment of the present invention, which provides a thermal body wrap, generally indicated as 10, preferably having a substantially planar laminate structure, and one or more heat cells 16 fixed within thermal pack 15. The laminate structure having a first side 12 and a second side 14. The first side 12, which is positioned toward the body during wear, having an attachment means 34, which is preferably located at or near first end 11 and/or second end 13. The second side 14, which is positioned away from the body during wear, having an oxygen permeability means for allowing oxygen into the heat cells 16.

As shown further in FIGS. 1 and 2, a preferred embodiment of the present invention, is substantially rectangular, dog bone-like shaped, with first end 11 and second end 13 at the respective terminuses of the longitudinal axis 21 of the thermal body wrap 10. A narrowing of the laminate structure at first edge 17 and second edge 19, approximately midway between first end 11 and second end 13, and the X-like positioning of heat cells 16 along longitudinal axis 21 allows the thermal body wrap to torsionally flex when applied to the user's body and/or worn by the user to provide conformity to the various areas of the body and/or body parts of the user. This particular shape also allows the user to apply the wrap to the user's bendable appendages without interfering with the user's ability to bend the respective appendage and/or cause the wrap to buckle and/or fold during normal movement of the user's appendage.

Each thermal pack 15 comprises a plurality of individual heat cells 16, preferably fixed within or to the unified structure of the thermal pack 15. While it is preferred that heat cells 16 are embedded within the laminate structure of thermal pack 15, each thermal pack 15 may alternatively comprise a single continuous base layer 20, wherein individual, or groups of heat cells 16 are fixedly attached and spaced apart across the base layer 20. These heat cells 16 are spaced apart from each other and each heat cell 16 functions independently of the rest of the heat cells 16. Each heat cell 16 preferably comprises a densely packed, particulate exothermic composition 18 which substantially fills the available cell volume within the cell reducing any excess void volume thereby minimizing the ability of the particulate matter to shift within the cell. Alternatively, the exothermic composition 18 may be compressed into a hard tablet before being placed in each cell. Because the heat generating material is densely packed or compressed into a tablet, the heat cells 16 are not readily flexible. Therefore, the spacing apart of the cells and the materials selected for cell forming base layer 20 and cell covering layer 22 between the heat cells 16 allows each thermal pack 15 to easily conform to the user's body more readily than a single large cell.

Continuous cell forming base layer 20 and cell covering layer 22 may be made of any number of suitable materials. Preferably cell forming base layer 20 and cell covering layer 22 comprises materials which are semirigid at a temperature of about 25° C. and which soften, i.e., become substantially less rigid, at a temperature of about 35° C., or greater. That is, the materials preferably have an elastic modulus, within the elastic deformation range of the material, of about 0.7 g/mm$^2$ or greater, more preferably about 0.9 g/mm$^2$ or greater, most preferably about 1 g/mm$^2$ or greater, at about 25° C. and an elastic modulus substantially less at about 35° C. or greater. "Substantially less", as used herein, means that the elastic modulus of the material at about 35° C., or greater, is statistically significantly less than the elastic modulus at about 25° C., at an appropriate statistical confidence (i.e.,>90%) and power (i.e.,>90%).

Therefore, when heat cells 16, which are fixed within or to the unified structure of thermal pack 15, are active, that is at a heat cell temperature of from about 35° C. to about 60° C., preferably from about 35° C. to about 50° C., more preferably from about 35° C. to about 45° C., and most preferably from about 35° C. to about 40° C., the narrow portion of the continuous layer or layers of material immediately surrounding each heat cell softens and acts as a hinge between the heat cells and between any remaining, cooler, more rigid portions of the continuous layer or layers, bending preferentially more than either the heat cell or more rigid portions. This results in thermal packs 15 which possess sufficient rigidity to maintain structural support of the heat cells and to prevent unacceptable stretching of structures of the continuous layer or layers during processing or use, while still maintaining good overall drape characteristics when heated.

When thermal pack 15 of the present invention is incorporated into body wrap 10, body wrap 10 easily adapts to a wide variety of body contours, provides consistent, convenient, and comfortable heat application, and an excellent conformity with body forms, while retaining sufficient rigidity to prevent wrap 10 from folding or bunching during use and deter easy access to heat cell contents.

Typically, the tensile strength is measured using a simple tensile test on an electronic tensile test apparatus, such as a universal constant rate elongation tensile testing machine with computer, Instron Engineering Corp., Canton, Mass. Any standard tensile test may be used, for example, material samples are cut into strips having a width of about 2.54 cm (about 1 inch) and a length of from about 7.5 cm to about 10 cm (about 3 to about 4 inches). The ends of the strips are placed into the jaws of the apparatus with enough tension to eliminate any slack, but without loading the load cell. The temperature of the sample is then allowed to stabilize at the desired test temperature. The load cell of the apparatus is set for about 22.7 kg (50 pound) load, the elongation set for 5 mm, and the crosshead speed is set for about 50 cm/min. The apparatus is started and the tensile strength data is collected by the computer. The sample is then removed from the apparatus.

The elastic modulus may be calculated as the slope of the tensile load vs. the extension during elastic deformation of the materials using the equation:

$$m = (L/E)$$

Where m=the slope in $g/mm^2$ during elastic deformation;

L=the load at extension in g/mm; and

E=the extension in mm.

Cell forming base layer 20 and/or cell covering layer 22 also preferably comprise at least two-dimensional drape at about 25° C., i.e., a single fold or crease occurs in the material along a single axis, and preferably three-dimensional drape at about 35° C. or greater, i.e., two or more folds or creases occur along multiple axes. Drape may be determined by placing and centering a square sample, for example about 30 cm by about 30 cm (about 12 inches by about 12 inches), of material on the end of a cylindrical shaft with a pointed end, allowing the material to drape due to gravitational forces, and the number of fold lines counted. Materials that exhibit one-dimensional drape, i.e., have no folds or creases in any direction, are determined to be rigid, while materials that exhibit at least two-dimensional drape, i.e., have at least one fold or crease line forming along at least one axis, are determined to be semirigid.

Different materials may be capable of satisfying the specified requirement for continuous cell forming base layer and/or cell covering layer 20 and/or 22 provided that the thickness is adjusted accordingly. Such materials may include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone, preferably extruded, more preferably coextruded, most preferably coextruded with a low melt temperature polymer including, but not limited to, ethylene vinyl acetate copolymer, low density polyethylene, and mixtures thereof.

Cell forming base layer 20 and/or cell covering layer 22 preferably comprise polypropylene, more preferably a coextruded material comprising polypropylene, most preferably a coextruded material wherein a first side comprises polypropylene, preferably from about 10% to about 90%, more preferably from about 40% to about 60%, of the total thickness of the material, and a second side comprises a tie-layer of a low melt temperature copolymer, preferably EVA. Cell forming base layer 20 and/or cell covering layer 22 preferably have a basis weight thickness of less than about 50 $\mu$m, more preferably less than about 40 $\mu$m, most preferably less than about 30 $\mu$m.

Cell forming base layer 20 and/or cell covering layer 22 preferably comprise a coextruded material, having a first side of polypropylene and a second side of EVA, and having a combined thickness of from about 20 $\mu$m to about 30 $\mu$m, preferably about 25 $\mu$m (1 mil), wherein the polypropylene comprises about 50% and the EVA tie-layer comprises about 50% of the total thickness of cell forming base layer 20 and/or cell covering layer 22. A particularly preferred material is available as P18-3161 from Clopay Plastics Products, Cincinnati, Ohio. The P18-3161 which is preferred for cell covering layer 22 has been subjected to a post process aperturing with hot needles to render it permeable to oxygen.

When coextruded materials of the type just described are used for cell forming base layer 20 and cell covering layer 22, the EVA sides are preferably oriented toward each other to facilitate thermal bonding of cell covering layer 22 to cell forming base layer 20.

Good overall drape characteristics and/or excellent conformity with user's body, and/or increased structural support to the thermal pack 15, and/or uniform distribution of the thermal energy across the entire area of the thermal body wrap may be achieved by selectively placing the heat cells 16 into positions fixed within or to the unified structure of the thermal pack 15 relative to each other which are sufficiently close so as to block some or all possible axes across the material of the continuous layer and/or layers 20 and/or 22, which otherwise would have passed uninterrupted between the heat cells 16, through the thermal pack 15, or select regions thereof, to minimize or eliminate undesirable, uninterrupted fold lines. That is, placement of the heat cells 16 into positions relative to each other which are sufficiently close so that the number of axes which pass uninterrupted, between the heat cells 16, is selectively controlled, such that the continuous cell forming base layer 20 and cell covering layer 22 of thermal pack 15, or select regions thereof, preferably folds along a multiplicity of short interconnected fold lines oriented in a number of different directions relative to each other. Folding along a multiplicity of interconnected fold lines results in thermal packs 15 which have good overall drape characteristics, readily conform with user's body, and/or have increased structural support of the heat cell matrix.

Because heat cells 16 are not readily flexible, the spacing between heat cells 16 provides the preferred benefits and may be determined, when selectively placing heat cells 16 within or fixed to the unified structure of thermal packs 15, wherein at least one heat cell of four adjacent heat cells, whose centers form a quadrilateral pattern, blocks one or more axes that could otherwise form at least one fold line tangential to the edges of one or more pairings of the remaining three heat cells in the quadrilateral pattern. Preferably, the spacing between the at least one heat cell of the four adjacent heat cells and each of the heat cells of the one or more pairings of the remaining heat cells in the quadrilateral pattern may be calculated using the equation:

$$s \leq (W_q/2)*0.75$$

Where s=the closest distance between the heat cells; and $W_q$=the measurement of the smallest diameter of the smallest diameter heat cell within the quadrilateral pattern.

Alternatively, the spacing between heat cells 16 may be determined wherein, at least one heat cell of three adjacent heat cells, whose centers form a triangular pattern, blocks one or more axes that could otherwise form at least one fold line tangential to the edges of the remaining pair of heat cells in the triangular pattern formed by the three heat cells. Most preferably, the spacing between the at least one heat cell of the three adjacent heat cells and each heat cell of the remaining pair of heat cells in the triangular pattern may be calculated using the equation:

$$s \leq (W_t/2)*0.3$$

Where s=the closest distance between the heat cells; and $W_t$=the measurement of the smallest diameter of the smallest diameter heat cell within the triangular pattern.

Different materials may be capable of satisfying the above specified requirements. Such materials may include, but are not limited to, those materials mentioned above.

Exothermic composition 18 may comprise any composition capable of providing heat. However, exothermic composition 18 preferably comprises a particulate mix of chemical compounds that undergo an oxidation reaction during use. The mix of compounds typically comprises iron powder, carbon, a metal salt(s), and water. Mixtures of this type, which react when exposed to oxygen, providing heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

The above-mentioned components of the composition are blended using conventional blending techniques. Suitable methods of blending these components are described in detail in U.S. Pat. No. 4,649,895 to Yasuki et al., issued Mar. 17, 1987.

Alternatively to the above described particulate exothermic composition, the exothermic composition may be formed into agglomerated granules, direct compacted into compaction articles such as granules, pellets, tablets, and/or slugs, and mixtures thereof The exothermic composition of these agglomerated granules and/or compaction articles comprises iron powder, dry powdered carbonaceous material, a metal salt added to the dry mix or subsequently as an aqueous/brine solution, in amounts and/or percentages and/or ratios as described above, and additionally an agglomeration aid, and/or a dry binder. Typically, the agglomeration aids comprise from about 0% to about 9%, preferably from about 0.5% to about 8%, more preferably from about 0.6% to about 6%, most preferably from about 0.7% to about 3% by weight; and the dry binder comprises from about 0% to about 35%, preferably from about 4% to about 30%, more preferably from about 7% to about 20%, most preferably from about 9% to about 15% by weight, of the agglomerated pre-compaction compositions of the present invention.

Agglomerated granules are typically made and agglomerated into granules using conventional blending techniques, as described above. Compaction articles are preferably made by direct compaction of the dry ingredients into articles such as hard granules, pellets, tablets, and/or slugs. Suitable methods are described in detail in Chapter 89, "Oral Solid Dosage Forms", *Remington's Pharmaceutical Sciences*, 18$^{th}$ Edition, (1990), pp. 1634–1656, Alfonso R. Gennaro, ed. Any conventional tableting machine and compression pressures, up to the maximum provided by the machine can be used.

Heat cells 16 comprising the above described components are typically formed by adding a fixed amount of a particulate exothermic composition or compaction article(s) 18 to a pocket or pockets made in a first continuous layer, i.e., cell forming layer 20. A second continuous layer, i.e., cell covering layer 22, is placed over the first continuous layer, sandwiching the particulate exothermic composition or compaction article(s) between the two continuous layers which are then bonded together, preferably using a low heat, forming a unified, laminate structure. Preferably, each heat cell has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

The heat cells 16 can have any geometric shape, e.g., disk, triangle, pyramid, cone, sphere, square, cube, rectangle, rectangular parallelepiped, cylinder, ellipsoid and the like. The preferred shape of the heat cells 16 is an ellipsoid (i.e., oval), having a width at its widest point of from about 0.15 cm to about 20 cm, preferably from about 0.3 cm to about 10 cm, more preferably from about 0.5 cm to about 5 cm, a height at its highest point of from greater than about 0.2 cm to about 5 cm, preferably from greater than about 0.2 cm to about 1 cm, more preferably from greater than about 0.2 cm to about 0.8 cm, and most preferably from about 0.3 cm to about 0.7 and a length at its longest point of from about 0.5 cm to about 20 cm, preferably from about 1 cm to about 15 cm, more preferably from about 1 cm to about 10 cm, most preferably from about 3 cm to about 7 cm.

The ratio of fill volume to cell volume of the heat cells 16 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability in cell covering layer 22 is preferably a plurality of apertures in cell covering layer 22. The apertures allow sufficient oxygen containing air to enter the cell to allow it to operate at the desired temperature.

The velocity, duration, and temperature of the thermogenic oxidation reaction of the exothermic composition 18 can be controlled as desired by changing the area of contact with air, more specifically, by changing the oxygen diffusion/permeability.

Preferably, each heat cell 16 has a similar volume of chemistry and has a similar oxygen permeability means. Alternatively, chemistry volumes, shapes, and oxygen permeability means can be different from cell to cell as long as the resulting cell temperatures generated are similar.

On either side of thermal body wrap 10 are additional layers of material. On first side 12 of thermal body wrap 10 is a first outer fabric 26, which is attached to cell forming base layer 20 by a first adhesive layer 28. On second side 14 is a second outer fabric 30 attached to cell covering layer 22 by a second adhesive layer 32. Second outer fabric 30 and second adhesive layer 32 are preferably more permeable to air than is cell covering layer 22, and preferably do not appreciably alter the oxygen permeability of cell covering layer 22. Therefore, cell covering layer 22 primarily controls the flow rate of oxygen into each heat generating cell 16. First outer fabric 26 and second outer fabric 30 may be made of different materials, however, it is preferred, first outer fabric 26 and second outer fabric 30 are made of the same or similar materials, and first adhesive layer 28 and second adhesive layer 32 are made of the same or similar materials. First outer fabric 26 and second outer fabric 30 may be laminate structures.

Preferably, first side 12 of thermal body wrap 10 has an attachment means 34 for releasably attaching thermal body wrap 10 to the user's body. Preferably attachment means 34 is an adhesive capable of attaching and reattaching to the user's skin. Attachment means 34 may have a release paper 36 attached to the adhesive in order to protect the adhesive of attachment means 34 from prematurely sticking to a target other than the intended attachment site. Attachment means 34 preferably has a stronger bond to first outer fabric 26 than to either release paper 36 or to any target surface.

In the alternative, attachment means 34 for releasably attaching thermal body wrap 10 to the user's body may be located on second side 14, or both first side 12 and second side 14.

Alternatively, attachment means 34 may be an adhesive coated film attached to first outer fabric 26.

Preferred attachment means 34, may be any number of suitable adhesives and application patterns. A preferred adhesive provides secure initial and prolonged attachment, reattachment, and easy/painless removal from the skin with substantially no residual adhesive remaining on the skin after removal of the wrap. Further, a preferred adhesive has a 90° peel strength of from about 300 g/25 mm to about 1000 g/25 mm, preferably form about 400 g/25 mm to about 90 g/25 mm, more preferably from about 500 g/25 mm to about 800 g/25 mm. Any suitable method may be used to measure the adhesive properties of the adhesive. However, a preferred method uses a steel platen wherein the adhesive film is attached to the surface of the platen. The steel platen and adhesive film are pulled in opposite directions at a 90° angle to the platen surface until the adhesive releases from the steel surface. The amount of force required to cause the adhesive to release from the steel surface is recorded as the peel strength. Several adhesive films have been shown useful in fulfilling these requirements, e.g., 5322 from Avery-Dennison Co., Painesville, Ohio; 1522 from Minnesota Mining and Manufacturing Co., Minneapolis, Minn.; and 9906 from Minnesota Mining and Manufacturing Co., Minneapolis, Minn. Other types of adhesives that may also be useful include, but are not limited to, rubber-based adhesives, e.g., styrene-butadiene-styrene (SBS), styrene-isoprene-styrene (SIS); polyurethane-based adhesives; acrylic-based adhesives; hydrogels; and the like. Adhesives may be applied to first outer fabric 26 by any suitable method. However, it is preferred that the adhesive penetrate into first outer fabric 26 so that the adhesive preferentially sticks to first outer fabric 26 upon removal of thermal body wrap 10 from the users body after use. The preferred pattern of adhesive extends from the terminus of first end 11 to the edge of heat cell 16 closest to first end 11, to first edge 17 and second edge 19, and/or from the terminus of second end 13 to the edge of heat cell 16 closest to second end 13, to first edge 17 and second edge 19, as depicted in FIG. 1. Other patterns may also be used as appropriate.

Release paper 36 is preferably a silicone treated paper, such as BL 25 MGA SILOX C3R/0 release paper from Akrosil, Menasha, Wis. or a similar silicone-treated paper from Avery-Dennison Co., Painesville, Ohio or Minnesota Mining and Manufacturing Co., Minneapolis, Minn. The release paper can be solely over the adhesive areas, slightly extended over the adhesive areas, or continuous across the entire wrap.

In a particularly preferred embodiment of the present invention, first outer fabric 26 is a soft, flexible, non-irritating-to-the-skin material. Materials suitable as first outer fabric 26 include but are not limited to: formed films; fabrics including wovens, knits, and nonwovens, which are carded, spunbonded, air laid, thermally bonded, wet laid, meltblown, and/or through-air bonded. The material of first outer fabric 26 may be cotton, polyester, polyethylene, polypropylene, nylon, etc. A particularly suitable material for first outer fabric 26 is 32 gsm polypropylene carded thermally bonded fabric available, e.g., as grade #9327786 from Veratec, Walpole, Mass. Laminates of these or similar materials may also be useful.

Preferably, second outer fabric 30 is preferably a soft flexible material. Materials suitable as second outer fabric 30 include, but are not limited to, formed films; fabrics including wovens, knits, and nonwovens, which are carded, spunbonded, air laid, thermally bonded, wet laid, meltblown, and/or through-air bonded. The material composition of second outer fabric 30 may be cotton, polyester, polyethylene, polypropylene, nylon, etc. A particularly suitable material for second outer fabric 30 is 32 grams per square meter (gsm), hydrophobic, polypropylene, carded thermal bonded fabric available, e.g., as grade #9327786 from Veratec, Walpole, Mass. Alternatively, second outer fabric 30 may be 65 grams per square meter (gsm), hydrophobic, polypropylene, carded thermal bonded fabric available, e.g., as grade #9354790 from Veratec, Walpole, Mass. Laminates of these or similar materials may also be useful.

Adhesive layer 32 is applied in such a manner that it does not interfere with oxygen permeability to heat cells 16. A suitable material and application method that has been successfully used for adhesive layers 28 and 32 are 70-4589 pressure sensitive hot melt adhesive available from National Starch and Chemical Co., Bridgewater, N.J., which is applied with spiral glue application system available from Nordson, Waycross, Ga.

Prior to use, thermal body wrap 10 is typically enclosed within an oxygen impermeable package. When ready to use, thermal body wrap 10 is removed from the oxygen impermeable package allowing oxygen to react with chemistry 18. Once the chemical reaction is completed, thermal body wrap 10 is no longer capable of generating heat and it is intended to be appropriately discarded in the solid waste system.

Thermal body wrap 10 is intended to be worn directly in contact with the user's body, inside a user's clothing. Such direct contact by heat cells 16 in the thermal body 10 provides a known thermal resistance between heat generating chemistry 18 and the user's body surface. Thus, the chemistry 18 can be designed to oxidise at a particular rate to produce a specified temperature.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal body wrap having a unified structure comprising:
   a) at least one continuous layer of flexible material having a substantially planar, rectangular shape, a first side, a second side, a longitudinal axis terminating at a first end and a diametric second end, a first edge and a second edge extending parallel to said longitudinal axis and terminating at said first end and said second end, and a narrowing of said continuous layer from said first edge to said second edge substantially midway between said first end and said second end;
   b) a plurality of heat cells containing an exothermic composition spaced apart and fixed within or to said at least one continuous layer of flexible material in a substantially X-like pattern along said longitudinal axis; and
   c) a means for releasably attaching said thermal body wrap to a user's body, said attachment means located at or near said first and second ends comprising an adhesive having secure initial and prolonged attachment, reattachment capability, and easy/painless removal from the skin with substantially no residual adhesive remaining on the skin after removal of said wrap.

2. A disposable thermal body wrap according to claim 1 wherein said means for releasably attaching said thermal body wrap being located on said first side of said flexible material so that said first side of said flexible material may be placed directly against a user's body, wherein said second side comprises an oxygen permeability means.

3. A disposable thermal body wrap according to claim 2 wherein said means for releasably attaching said thermal body wrap comprises an adhesive having a 90° peel strength of from about 300 g/25 mm to about 1000 g/25 mm.

4. A disposable thermal body wrap according to claim 1 wherein said heat cells comprise a shape selected from the group consisting of a disk, triangle, pyramid, cone, sphere, square, cube, rectangle, rectangular parallelepiped, cylinder, and ellipsoid, said ellipsoid having a width at its widest point of from about 0.3 cm to about 10 cm and a height at its highest point of from greater than about 0.2 cm to about 5 cm and a length at its longest point of from about 1 cm to about 10 cm, and wherein said heat cells, when filled with said exothermic composition, have a fill volume to cell volume ratio of from about 0.7 to about 1.0.

5. A disposable thermal body wrap according to claim 1 wherein said exothermic composition comprises:
   a.) from about 30% to about 80% by weight, iron powder;
   b.) from about 3% to about 25% by weight, carbonaceous material selected from the group consisting of activated carbon, non-activated carbon, and mixtures thereof;
   c.) from about 0.5% to about 10% by weight, metal salt; and
   d.) from about 1% to about 40% by weight, water.

6. A disposable thermal body wrap according to claim 5 wherein said exothermic composition further comprises from about 0.1 to about 30% by weight, of additional water-holding material.

7. A disposable thermal body wrap according to claim 1 wherein said exothermic composition comprises:
   a.) from about 30% to about 80% by weight, of iron powder;
   b.) from about 3% to about 20% by weight, of carbonaceous material selected from the group consisting of activated carbon, non-activated carbon, and mixtures thereof;
   c.) from about 0% to about 9% by weight, of an agglomeration aid selected from the group consisting of corn syrup, maltitol syrup, crystallizing sorbitol syrup, amorphous sorbitol syrup, and mixtures thereof; and
   d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof; wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof, wherein said direct compaction articles are selected from the group consisting of granules, pellets, tablets, and slugs.

8. A disposable thermal body wrap according to claim 7 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

9. A disposable thermal body wrap according to claim 8 wherein said dry binder comprises from about 4% to about 30% by weight, of microcrystalline cellulose.

10. A disposable thermal body wrap according to claim 1 further comprising additional components selected from the group consisting of active aromatic compounds, non-active aromatic compounds, pharmaceutical actives, and mixtures thereof.

11. A disposable thermal body wrap according to claim 1 wherein the spacing between said at least one of said beat cells and each of said heat cells of said one or more pairings of said remaining beat cells in said quadrilateral pattern is the same or less than the spacing obtained by dividing the measurement of the smallest diameter of the smallest diameter heat cell of said heat cells within said quadrilateral pattern by 2 and multiplying the result by 0.75.

12. A disposable thermal body wrap according to claim 1 wherein the spacing between said at least one of said heat cells and each of said heat cells of said remaining pair of said heat cells in said triangular pattern is the same or less than the spacing obtained by dividing the measurement of the smallest diameter of the smallest diameter heat cell of said heat cells within said triangular pattern by 2 and multiplying the result by 0.3.

* * * * *